(12) United States Patent
Bilali

(10) Patent No.: US 6,169,118 B1
(45) Date of Patent: Jan. 2, 2001

(54) FLAVOR BLEND FOR MASKING UNPLEASANT TASTE OF ZINC COMPOUNDS

(75) Inventor: Essat Bilali, Palisade Park, NJ (US)

(73) Assignee: Block Drug Company, Inc., Jersey City, NJ (US)

(*) Notice: Under 35 U.S.C. 154(b), the term of this patent shall be extended for 0 days.

(21) Appl. No.: 09/434,334

(22) Filed: Nov. 4, 1999

Related U.S. Application Data

(60) Provisional application No. 60/108,212, filed on Nov. 12, 1998.

(51) Int. Cl.$^7$ ................................................ A61K 33/30
(52) U.S. Cl. .................... 514/974; 424/49; 424/401; 424/464; 514/494; 514/849
(58) Field of Search ................................................ 424/49

(56) References Cited

U.S. PATENT DOCUMENTS

| 4,684,528 | 8/1987 | Godfrey | 426/74 |
|---|---|---|---|
| 4,758,439 | 7/1988 | Godfrey | 426/74 |
| 5,002,970 * | 3/1991 | Eby, III | 514/494 |
| 5,095,035 | 3/1992 | Eby | 514/494 |
| 5,700,449 * | 12/1997 | Katayama et al. | 424/49 |
| 5,766,622 | 6/1998 | Nelson | 424/440 |
| 5,817,295 | 10/1998 | Chaudhari et al. | 424/49 |

FOREIGN PATENT DOCUMENTS

| 049 671 | 4/1982 | (EP) . |
|---|---|---|
| 1055854 | 5/1965 | (GB) . |
| 59-101418 | 12/1984 | (JP) . |
| 63-066115 | 3/1988 | (JP) . |

* cited by examiner

*Primary Examiner*—Shelley A. Dodson
*Assistant Examiner*—Konata M. George

(57) ABSTRACT

A synergistic flavoring combination of at least two flavoring oils and lauryl alcohol for use in an orally administered formulation which contains an ionizable zinc compound having an undesirable taste, the flavoring combination is unexpectedly effective in masking the unpleasant taste or aftertaste of zinc.

20 Claims, No Drawings

FLAVOR BLEND FOR MASKING UNPLEASANT TASTE OF ZINC COMPOUNDS

This is based on provisional patent application No. 60/108,212, filed Nov. 12, 1998.

BACKGROUND OF THE INVENTION

1. Field of Invention

This invention relates to a flavoring method and flavor composition for masking flavor and taste of compositions for oral absorption and administration by humans which contain zinc compounds.

2. General Background

The value of the element zinc is well-established. Zinc has a vital role in a number of pharmaceutical formulations. Zinc deficiency is an important feature of many cases of sickle cell anemia characterized by growth retardation and hypogonadism, and zinc appears to have an antisickling effect. Zinc has also been shown to be beneficial in the relief of acute inflammatory conditions associated with rheumatoid arthritis. Use of zinc gluconate and zinc acetate has been described as a method for reducing duration of common cold symptoms. Zinc oxides are used in a number of dental products such as dentifrices, denture adhesives, dental fillings, dental cements, and dental impression materials. Zinc salts are generally reported to enhance activity of triclosan and cationic anti-microbials in dentifrices and mouthwashes. Zinc chloride has been recognized as possessing anti-odor properties in oral health care products. Zinc citrates are useful in reducing dental calculus formation.

In recent years, formulations for oral administration and/or absorption such as tablets, powders, lozenges, syrups, sprays, dentifrices, mouthwashes, etc. have been formulated containing a zinc component. One of the major drawbacks of the incorporation of zinc compounds into various orally absorbed or administered products has been the characteristic bitterness of zinc that is experienced as soon as the zinc compound is released and proceeds to break down in the mouth. A variety of formulations and methods have been prepared and attempted to lessen or mask entirely the bitter taste and aftertaste of zinc compounds.

U.S. Pat. Nos. 4,684,528 and 4,758,439 disclose the formulation of zinc compounds with glycine and certain other amino acids to reduce the unpalatable and undesirable aftertaste of prior zinc formulations. U.S. Pat. No. 5,095,035 teaches masking compositions which contain zinc acetate with the addition of extramolar citric acid. U.S. Pat. No. 5,002,970 discloses that ionizable zinc compounds can be masked with anethole to eliminate or reduce the taste and after taste of zinc. U.S. Pat. No. 5,766,622 teaches the use of phosphorylated amino acid in oral compositions to inhibit bitter and/or metallic taste from a pharmaceutical active component. U.S. Pat. No. 5,817,295 discloses a tripartite blend of peppermint oils that provides for a pleasant tasting mouthwash and masking the bitter taste of essential oils used for antimicrobial efficacy in the mouthwash.

There is still a need for a new way to eliminate the objectionable taste and after taste of zinc compounds using new technologies.

SUMMARY OF THE INVENTION

The present invention relates to an orally administered formulation comprising about 0.1 to 25 wt. % of an ionizable zinc compound having an undesirable taste, and a synergistic flavoring combination of at least two flavoring oils and lauryl alcohol in an amount effective to mask the undesirable taste of said ionizable zinc compound.

The invention also provides a method for improving the taste of an orally administered formulation containing about 0.1 to 25 wt. % of an ionizable zinc compound with undesirable taste, by mixing into said formulation a synergistic flavoring combination of at least two flavoring oils and lauryl alcohol in an amount effective to mask the undesirable taste of said ionizable zinc.

DESCRIPTION OF THE INVENTION

The present invention provides an orally administered formulation containing an ionizable zinc compound with undesirable taste, but without the unpleasant metallic taste of zinc. The formulation can be in the form of foods, pharmaceuticals, toiletries, etc. The formulation contains an insoluble zinc compound and a carrier medium making up the balance.

Zinc Compounds. The orally administered formulations may contain one or more insoluble zinc compounds depending on the application. Zinc compounds include both inorganic and organic zinc salts and, in particular, salts such as the halides, nitrates, sulfates, chromates, silicates, and compounds comprising complexes of these materials constituting the inorganic salts contemplated herein. Organic salts of zinc include but not limited zinc gluconate, zinc formate, zinc succinate, zinc aspartate and the like. Particular zinc halides include zinc chloride, zinc bromide, zinc fluoride, and mixtures.

In terms of specific applications, typical zinc compounds used in dental formulations include such materials as zinc oxide for use in inhibiting bacterial attack in dentifrices. Zinc oxide is also used as a binding materials in denture adhesives. Zinc chloride and zinc citrate are used as anti-odor ingredients in dental formulations. Zinc acetate and hydroxide is used for their anti-plaque properties. Zinc citrate, polyphospohates such as disodium ethane-1-hydroxy-1,1-diphosphonate (EHDP), pyrophosphate, tetrametaphosphate, metaphosphate and orthophosphate salts of zinc for tartar removal effects in dentifrices. Zinc glycerophosphate, zinc phenolsulfonate, zinc fluorosilicate, zinc fluorozirconate are known for their astringent and deodorant capabilities. Zinc citrate is preferred for dental formulations. Zinc acetate and zinc gluconate are favored in compositions for treating common colds.

In general, the concentration of zinc compounds in orally administered formulations varies from about 0.1 to 15 wt. %. The concentration can range up to as much as 25% depending on the particular formulation in which the zinc compound is incorporated. A more preferred amount is about 0.2 to 2 wt. %. A most preferred amount is from about 0.5 to 2 wt. %.

Flavoring/masking components: The taste masking/flavoring combination of the present invention is made up of a mixture of flavoring oils and lauryl alcohol.

For the purpose of this invention, flavoring oils used herein refer to both entire essential oils and the aroma chemicals making up the essential oils. Esential oils are predominately volatile materials from botanical sources. The most widely used process for the isolation of essential oils is steam distillation of plant matter, although dry distillation and solvent extraction are also used. Essential oils are generally recognized as safe compositions that can be included in ingested materials. Aroma chemicals refer to chemicals which may be synthetic or natural, derived from essential oils, i.e., derived from plants by distillation, expression, or extraction, and which usually carry the flavor of the plant from which they are derived.

Although the invention is not limited to the specific essential oils listed individually in this specification, a number of important essential oils include spearmint oil; peppermint oil; wintergreen oil; lavender oil; sassafras oil; ginger oil; clove oil; sage oil; basil oil; eucalyptus oil; laurel oil; mayonara oil; cinnamon oil; chamomile oil; thyme oil; citrus oils such as lemon oil, orange oil, grapefruit oil, tangerine oil; oil of anise; camphor oil; and the like.

Aroma chemicals include but not limited to anethole, carvone, cintronellal, camphor, linalool, menthol, menthone, thymol, and the like.

It has been found that in an orally administered formulation of the claimed invention, the additional presence of lauryl alcohol in combination with a mixture of flavoring oils as a flavoring composition, enhances the organoleptic properties, imparts freshness in the mouth and masks the unpleasant taste and aftertaste of the zinc compound in the formulation. The flavoring oils appear to be operating in synergistic combination, perhaps with the lauryl alcohol or perhaps because of the ability of various components of the flavoring oils themselves to inhibit different biological pathways associated with bioavailability.

The individual flavoring oils can be mixed and matched as desired to provide the intended flavor in the orally administered composition. The concentrations of the individual components can therefore vary quite widely. It is preferred, nevertheless, that the flavoring oils in total will be about 80–99.5 wt. % of the synergistic taste masking/flavoring combination, and most preferred about 95–99%. The lauryl alcohol makes up the rest of the masking/flavoring combination.

In general, the synergistic taste masking/flavoring combination is present in an amount of about 0.1 to 5 wt. % of the orally administered formulation. A preferred amount is about 0.1–3% wt. %. A most preferred amount is from about 0.1 to 2 wt. %.

Carriers & Other Ingredients: The carriers vary according to the applications. In toothpastes it is desirable to employ thickening agents such as hydroxyethylcellulose and water-soluble salts of cellulose ethers, including sodium carboxymethyl cellulose and sodium carboxymethylhydroxyethyl cellulose; or natural gums, including gum karaya, gum arabic, and gum tragacanth. Also, colloidal magnesium aluminum silicate or finely divided silica can be used as part of the thickening agent to improve the texture of the product. Thickening agents are used at levels of from 0.1% to 5.0% of the toothpaste composition. It is also desirable to include a humectant material in toothpastes. Suitable materials for this purpose include glycerine, sorbitol, and other edible polyhydric alcohols or mixtures thereof. These materials can comprise from about 1% to about 50% of the toothpaste composition. Dentifrices normally also contain sweetening agents. Suitable sweetening agents for use in dentifrices include for example saccharin, dextrose and levulose. The sweetening agents are used at levels of from about 0.05% to about 2%. In addition to the aforementioned typical components of a toothpaste, water usually comprises the balance of the toothpaste, and is usually present at levels up to about 50%.

Mouthwashes generally comprise a water/ethyl alcohol solution and optionally other ingredients such as sweeteners, and humectants such as those mentioned above for dentifrices. The alcohols provide an antibacterial effect and help the solubility of the flavoring oils. Optionally, mouthwashes also contain sudsing agents. Humectants such as glycerine and sorbitol give a moist and sweet feel in the mouth and are desirably also present. While these materials are not always essential, they are useful to help solubilize and chance the flavoring oils, and aid in making the product sweet, smoother and imparting body. Antibacterial agents are sometimes incorporated into mouthwashes or dentifrices at levels from about 0.01% to about 2.0%. Generally, mouthwashes suitable for use as carriers herein contain: 5% to 40% ethyl alcohol; 0% to 20%, preferably 5% to 20%, glycerine or other humectant; 0% to 12%, preferably 0.1% to 12%, sudsing agent, 0% to 0.5%, preferably 0.05% to 0.5%, sweetening agent such as saccharin; and 0% to 0.3%, preferably 0.05% to 2% of the flavoring/masking components of the present invention; and the balance, water with colorants or dyes if desired.

Chewing gum suitable for use as a carrier herein comprises a gum base and flavoring materials such as those mentioned above for dentifrices. The flavoring materials are present at a level of 0.01% to about 2.0% of the final chewing gum composition. The gum base is a chewable plastic gum material such as natural rubber, chicle, polyvinyl acetate, ester gum, coumarone resin, and paraffin wax. The gum base is typically made from a mixture of two or more plastic gum materials to achieve a preferred degree of plasticity for chewing. Optionally, corn syrup is added as a softener and binder for the chewing gum and sugar is optionally added as a filler and sweetener and adding nuance to the flavor. A typical chewing gum suitable as a carrier herein comprises 15% to 30% gum base, 15% to 20% corn syrup, 50% to 65% sugar, 1% of zinc gluconate trihydrate, and 0.05% to 1.5% of the flavoring/masking composition of the invention.

Lozenges suitable as carriers herein comprise a hard sugar candy base and one or more flavoring oils. Optionally, lozenges can contain various other materials. A typical lozenge suitable as a carrier in this invention is a hard candy comprised of a hard candy base containing 0.05% to 1.5 wt. % of the flavoring/masking components and about 1 wt. % of zinc acetate dihydrate. The hard candy base is a solidified solution of amorphous sugar which is generally formed from a sugar solution which has been cooked at high temperature so as to remove nearly all of the moisture. The taste masking/flavoring materials are added before the moisture is removed.

The orally administered compositions of the present invention can also optionally contain additional therapeutic materials including for example, water-soluble fluoride such as sodium fluoride and stannous fluoride.

Preparations: The orally administered compositions of the present invention without the metallic zinc taste can be prepared by any convenient method. The individual components of the synergistic masking/flavoring composition can be added separately as separate components to the orally administered compositions, but it is generally preferred to prepare the masking/flavoring composition separately and thereafter combine it with the orally administered compositions.

The orally administered compositions of the present invention can be in solid forms such as tablets, lozenges and powders; chewable forms such as chewing gums and soft candies; paste and gel forms such as dentifrices; liquids such as syrups, mouthwashes, and sprays. Flavored lozenges with zinc compounds can be prepared by mixing the masking components of the present invention with the carriers and other ingredients, then by direct compression of the ingredients.

When the compositions are applied to or in contact with oral and oral pharyngeal membranes of a human, they are palatable and without undesirable taste or unpleasant metallic taste of zinc compounds. The flavors produced are truer, smoother, and better in taste than formulations without the masking/flavoring components of the present invention. In order to further illustrate the present invention, examples are set forth below. All parts and percentages are by weight and all temperatures in degrees in centigrade unless otherwise indicated.

Various flavoring compositions were prepared by mixing the components (in wt. %) set forth in Table 1 that follows:

TABLE 1

|  | Example 1 | Compare 1 | Compare 2 | Example 2 |
| --- | --- | --- | --- | --- |
| 1-Menthol | 31.3 | 13.9 | 9 | 35.4 |
| Peppermint Oil | 24.3 | 27.8 | 54 | 25.3 |
| 1-Carvone | 21.5 | 17.6 | — | 29.3 |
| Spearmint Oil 50/50 | 18.0 | 32.4 | 17 | 5 |
| Anethole | 3.5 | 8.3 | — | 4 |
| Lauryl Alcohol, C-12 | 1.4 | — | — | 1 |
| Optiacool A | — | — | 20 | — |

The flavor compositions were combined into a dentifrice composition containing the following components:

TABLE 2

| Ingredients | Parts By Weight |
| --- | --- |
| Sorbitol Solution | 27 |
| Glycerine | 10 |
| Amorphous Silica | 10 |
| Cocamidopropyl Betaine | 4 |
| KCl | 3.75 |
| Zinc Citrate | 2 |
| Colloidal Silica | 1.7 |
| Sodium Carboxymethyl Cellulose | 1.6 |
| Flavor Blend | 1 |
| Titanium Dioxide | 0.5 |
| Carboxymethyl Cellulose | 0.4 |
| Sodium Saccharine | 0.4 |
| Sodium Fluoride | 0.3 |
| Trisodium Phosphate | 0.2 |
| Water | Qs to 100 |

In blind taste tests, it is found that the dentifrice compositions containing the masking/flavoring compositions in the Examples exhibit "good tasting" properties and without any trace of the unpleasant metallic taste of zinc compounds.

Various changes and modifications can be made in the products of the present invention without departing from the spirit and scope thereof the various embodiments which were disclosed herein were for the purpose of further illustrating the invention but were not intended to limit it.

What is claimed is:

1. An orally administered formulation that releases zinc ions to the oral and oral pharyngeal mucous membranes of a human comprising a suitable carrier and uniformly contained in said formulation:
   about 0.1 to 25 wt. % of an ionizable zinc compound having an undesirable taste;
   a synergistic flavoring combination of at least a flavoring oil and lauryl alcohol in an amount effective to mask the undesirable taste of said ionizable zinc compound.

2. The orally administered formulation of claim 1, wherein the lauryl alcohol is present in an amount of about 0.5–20 wt. % of the synergistic flavoring combination.

3. The orally administered formulation of claim 1, wherein said flavoring oil is selected from the group consisting of: peppermint oil, spearmint oil, carvone, anethole and mixtures thereof.

4. The orally administered formulation of claim 1, wherein said ionizable zinc compound is selected from the group consisting of: zinc oxide, zinc citrate, zinc chloride, zinc acetate, zinc hydroxide, zinc fluorosilicate, zinc fluorozirconate, zinc acetate, zinc gluconate and mixtures thereof.

5. The orally administered formulation of claim 4, wherein said ionizable zinc compound is zinc citrate.

6. The orally administered formulation of claim 1, in the form of a dentifrice.

7. The orally administered formulation of claim 1, in the form of a lozenge.

8. The orally administered formulation of claim 1 in the form of a mouth rinse.

9. The orally administered formulation of claim 1 the form of a chewable tablet.

10. The orally administered formulation of claim 1, in the form of a syrup.

11. The orally administered formulation of claim 1, selected from the group consisting of foods, pharmaceuticals, and mixtures thereof.

12. A method for improving the taste of an orally administered formulation, which formulation includes about 0.1 to 25 wt. % of an ionizable zinc compound with undesirable taste, said method comprising mixing a synergistic flavoring combination of at least a flavoring oil and lauryl alcohol in an amount effective to mask the undesirable taste of said ionizable zinc.

13. The method of claim 12, wherein the lauryl alcohol is present in an amount of about 0.5–20 wt. % of the synergistic flavoring combination.

14. The method of claim 12, wherein said flavoring oil is selected from the group consisting of: peppermint oil, spearmint oil, carvone, anethole and mixtures thereof.

15. The method of claim 12, wherein said ionizable zinc compound is selected from the group consisting of: zinc oxide, zinc citrate, zinc chloride, zinc acetate, zinc hydroxide, zinc fluorosilicate, zinc fluorozirconate, zinc acetate, zinc gluconate and mixtures thereof.

16. The method of claim 12, wherein said orally administered formulation is selected from the group consisting of food pharmaceuticals, toiletries, and mixtures thereof.

17. A preformulation consisting essentially of about 80–99.5 wt. % of at least a flavoring oil and about 0.5 to 20 wt. % lauryl alcohol, wherein said preformulation when uniformly mixed in an orally administered formulation containing about 0.1 to 25 wt. % of an ionizable zinc compound with undesirable taste, masks the undesirable taste of said ionizable zinc compound.

18. The preformulation of claim 17, wherein said said flavoring oil is selected from the group consisting of: peppermint oil, spearmint oil, carvone, anethole and mixtures thereof.

19. The preformulation of claim 17, wherein said orally administered formulation is selected from the group consisting of foods, pharmaceuticals, and mixtures thereof.

20. The preformulation of claim 17, wherein said ionizable zinc compound is selected from the group consisting of: zinc oxide, zinc citrate, zinc chloride, zinc acetate, zinc hydroxide, zinc fluorosilicate, zinc fluorozirconate, zinc acetate, zinc gluconate and mixtures thereof.

* * * * *